United States Patent [19]

Purkait et al.

[11] Patent Number: 5,019,101
[45] Date of Patent: May 28, 1991

[54] SELF-SEALING VALVE FOR IMPLANTABLE DEVICE

[76] Inventors: Bobby K. Purkait, 649A Verd Mar Dr., Santa Barbara, Calif. 93103; Hilton Becker, 4417 Woodfield Blvd., Boca Raton, Fla. 33434

[21] Appl. No.: 359,481

[22] Filed: May 31, 1989

[51] Int. Cl.$^5$ .............................................. A61F 2/12
[52] U.S. Cl. ........................................ 623/8; 604/93; 604/256; 137/223
[58] Field of Search ............... 623/8, 14; 604/93, 256; 137/855, 223

[56] References Cited

U.S. PATENT DOCUMENTS

| | | |
|---|---|---|
| 564,502 | 7/1896 | Brookes . |
| 1,008,641 | 11/1911 | Gregory . |
| 1,551,099 | 8/1925 | Goldsmith et al. . |
| 2,142,414 | 1/1939 | Riddell ................... 273/65 |
| 2,516,129 | 7/1950 | Leo et al. ................. 2/42 |
| 2,568,976 | 9/1951 | Andrews ............. 251/119 |
| 2,697,229 | 12/1954 | Krueger ................. 2/267 |
| 2,700,980 | 2/1955 | Andrews ............... 137/223 |
| 2,795,425 | 6/1957 | Orms ..................... 273/58 |
| 2,826,523 | 3/1958 | Blaszkowski et al. .......... 154/50 |
| 2,933,120 | 4/1960 | Siedow .................. 152/429 |
| 3,204,959 | 9/1965 | Nicholls ................. 273/58 |
| 3,410,300 | 11/1968 | Mondano ............. 137/223 |
| 3,523,563 | 8/1970 | Mirando ............... 141/313 |
| 3,565,078 | 2/1971 | Vaillancourt ......... 128/349 |
| 3,584,671 | 6/1971 | Kampa .................. 152/429 |
| 3,600,718 | 8/1971 | Boone ..................... 623/8 |
| 3,852,832 | 12/1974 | McGhan et al. ........... 3/36 |
| 3,852,833 | 12/1974 | Koenke et al. ............ 3/36 |
| 3,919,724 | 11/1975 | Sanders et al. ........... 3/36 |
| 4,178,643 | 12/1979 | Cox, Jr. .................. 3/36 |
| 4,263,682 | 4/1981 | Bejarano ................ 623/8 |
| 4,433,440 | 2/1984 | Cohen ..................... 3/36 |
| 4,459,318 | 7/1984 | Hyans .................... 427/36 |
| 4,662,883 | 5/1987 | Bell et al. ................ 623/8 |
| 4,775,379 | 10/1988 | Fogarty et al. ........... 623/8 |
| 4,930,535 | 6/1990 | Rinehold ................. 623/8 |

FOREIGN PATENT DOCUMENTS 9698 of 1902 United Kingdom .

Primary Examiner—Randall L. Green
Assistant Examiner—Stephanie L. Iantorno
Attorney, Agent, or Firm—Kinney & Lange

[57] ABSTRACT

A valve for use in a fluid fillable and implantable device in cooperation with a fill tube includes a main body portion having a channel for receiving the fill tube and wherein the main body portion has an unevenly stressed section that includes a selected section of the channel and wherein the unevenly stressed section is stressed so that the selected section of the channel folds back occluding the channel when the fill tube is withdrawn. The valve also includes a gel-filled chamber in which the main body portion is disposed. The main body portion includes a free end that is occluded by the gel once the fill tube has been withdrawn from the fill tube channel.

8 Claims, 3 Drawing Sheets

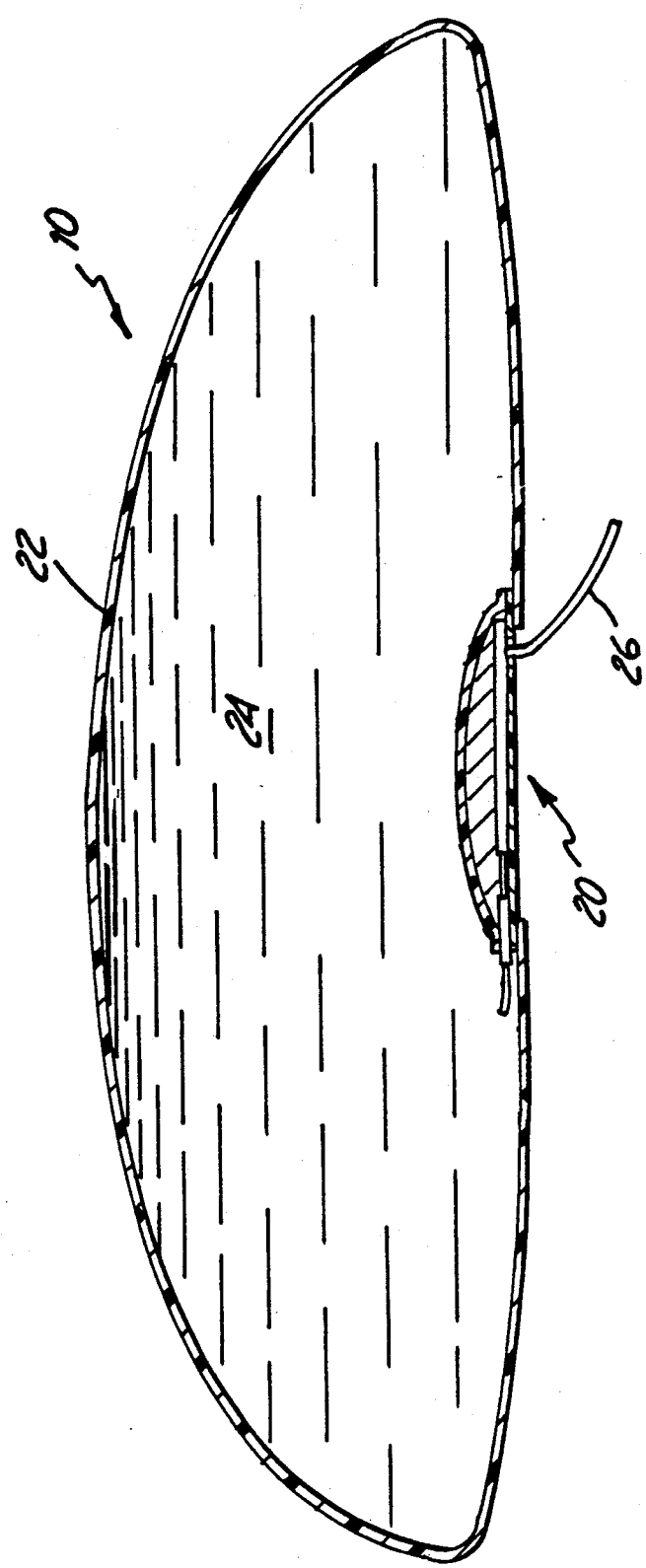

SELF-SEALING VALVE FOR IMPLANTABLE DEVICE

BACKGROUND OF THE INVENTION

The present invention relates to self-sealing valves, and in particular, it relates to self-sealing valves for use in implantable devices.

In recent developments in inflatable prosthetic devices, it has been found desirable to progressively inflate the prosthetic device over a period of time. This has required the use of subcutaneous injection sites connected to the inflatable prosthetic device by a fill tube.

Implantable devices that are used both as a skin expander and a breast prosthesis have become increasingly popular. Initially, this type of expander/prosthesis is implanted in a deflated state in a pocket surgically made in the breast area. The device includes an inflatable chamber, and a subcutaneously implanted injection site which is connected to the inflatable chamber through a fill tube. The fill tube is connected to the inflatable chamber by a valve which has the ability to seal once the fill tube is pulled.

Once the expander/prosthesis is filled to a desired inflation level or the amount of skin expanded reaches a desired level, the fill tube is pulled out of the valve and is removed from its subcutaneous location along with the injection site. Upon removal the valve must seal and the expander now acts as a prosthesis. The key to such a device functioning properly is the ability of the valve to seal once the fill tube is removed, such that there is absolutely no leakage.

The prior art valves that have been used in such prostheses, although providing a seal, do not provide an absolute seal since some leakage can occur. It will be appreciated that although the leakage rate is slight, and not noticeable over a short period of time, any decrease in fluid volume in the prosthesis over several years is unacceptable.

A practical aspect of implantation of such devices is that from the time the device is manufactured to the time that the fill tube is pulled from the valve may be two years or more. It has been found that stresses are placed in the valve material which surrounds the fill tube to an extent that such material does not relax back to its original (closed) position and therefore does not provide an absolute seal once the fill tube is removed.

One type of valve that has been used is made of two sheets of silicone elastomer bonded together along edge portions to form a passage between the bonded edge portions. A fill tube is typically inserted within the passage. If the fill tube is in the passage for any length of time, the silicone rubber around the passage area is stressed, resulting in the valve not sealing adequately once the fill tube is removed. The passage becomes somewhat "set" over time and cannot return to its original position once the fill tube has been removed.

A curling self-sealing valve is described in Bell et al U.S. Pat. No. 4,662,883 entitled "Self-sealing Valve for Fluid Fillable Device" that provides a seal by curling along the longitudinal axis of the fill tube passage.

Another self-sealing valve for fluid fillable article is disclosed in the Fogerty et al U.S Pat. No. 4,775,379. The valve in the Fogerty et al patent has a passage portion which is flanked on opposing sides by first and second portions of elastomeric material. The passage portion is in a stretched state relative to the first and second portions so that the passage portion curls along the passage when the fill tube is removed.

The Boone patent describes an implantable mammary prosthesis including an inflatable shell and a filling stem. At the point of introduction of the stem into the shell, the stem passes through a capsule of sealing gel. After implantation and inflation, the stem is withdrawn either wholly or partially and gel in the capsule seals the stem outlet against leakage of the inflating fluid.

A number of other patents directed to prosthetic inflatable devices show valves which are constructed of two sheets of silicone elastomer bonded together along two edges to form a passage. None of the valves illustrated in the immediately below-listed patents are constructed to avoid the passage being permanently deformed due to the stress caused by the fill tube being present in the passage over a long period of time:

| Inventor | Pat. No. |
| --- | --- |
| Hyans | U.S. 4,459,318 |
| Bejarano | U.S. 4,263,682 |
| Cox, Jr. | U.S. 4,178,643 |
| Koneke et al | U.S. 3,852,833 |
| McGhan et al | U.S. 3,852,832 |
| Valliancourt et al | 3,565,078 |
| Krueger | 2,697,229 |

Other patents describe yet different valve arrangements in breast prosthesis:

| Inventor | U.S. Pat. No. |
| --- | --- |
| Cowen | 4,433,440 |
| Boone | 3,600,718 |
| Leo et al | 2,516,129 |

A number of other patents show inflatable devices other than prosthetic devices that include a variety of valving arrangements for the introduction of air. However, these valves in the immediately below-listed patents are also not designed for the retention of a fill tube for a long period of time.

| Inventor | Pat. No. | |
| --- | --- | --- |
| Kampa | U.S. | 3,584,671 |
| Mirando | U.S. | 3,523,563 |
| Mondano | U.S. | 3,410,300 |
| Nicholls | U.S. | 3,204,959 |
| Siedow | U.S. | 2,933,120 |
| Blaszkowski et al | U.S. | 2,826,523 |
| Orms | U.S. | 2,795,425 |
| Andrews | U.S. | 2,700,980 |
| Andrews | U.S. | 2,568,976 |
| Riddell | U.S. | 2,142,414 |
| Goldsmith et al | U.S. | 1,551,099 |
| Gregory | U.S. | 1,008,641 |
| Brookes | U.S. | 564,502 |
| Ingram | U.K. | 9,698 |
| Tomkins | French | 719,244 |

SUMMARY OF THE INVENTION

The present invention includes a valve having a main body portion with a channel for receiving a fill tube. The main body portion includes first and second elastomeric layers which define the channel for receiving the fill tube and wherein one portion of an elastomeric layer is restrained while a portion of a second elastomeric layer is unrestrained such that the main body portion flexes in the area of the unrestrained second elastomeric layer to an extent that the channel is occluded.

The present invention also includes a valve having a gel chamber in which the main body portion is disposed. The main body portion has a free end which is occluded with gel once the fill tube is withdrawn from the fill tube channel.

BRIEF DESCRIPTION OF THE DRAWINGS

FIG. 1 is a cross sectional view of the valve of the present invention in an expander/prosthesis.

DETAILED DESCRIPTION OF THE PREFERRED EMBODIMENTS

Figure 4:
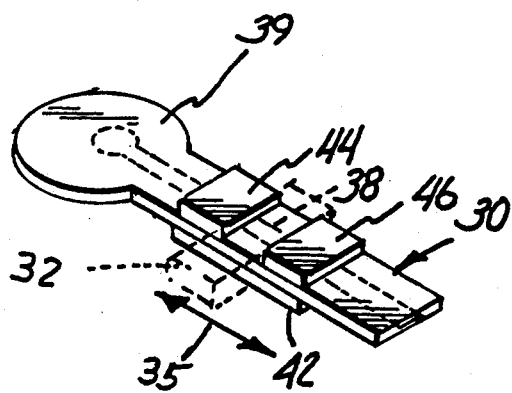
FIG. 4 is a perspective view of a portion of the valve of the present invention.

A skin expander/mammary prosthesis generally indicated at 10 incorporating the valve 20 of the present invention is illustrated in FIG. 1. The prosthesis 10 includes an outer shell 22 defining an inflation chamber 24. A fill tube 26 extends through the valve 20 into the chamber 24 providing access for fluid to flow into or out of the chamber 24. Fluid is provided through a subcutaneous injection site (not shown) connected to the fill tube. Although a single chamber expander/prosthesis is illustrated, it is understood that the valve of the present invention can be used in multiple chambered prostheses. For example, in a double-chambered mammary prosthesis, two valves would be used, a first valve providing access through the inner shell and a second valve providing access through the outer shell. A common fill tube can extend through each of the valves, such as is described in the Bell et al U.S. Pat. No. 4,662,883, or a separate fill tube can extend through each of the valves.

Figure 2:
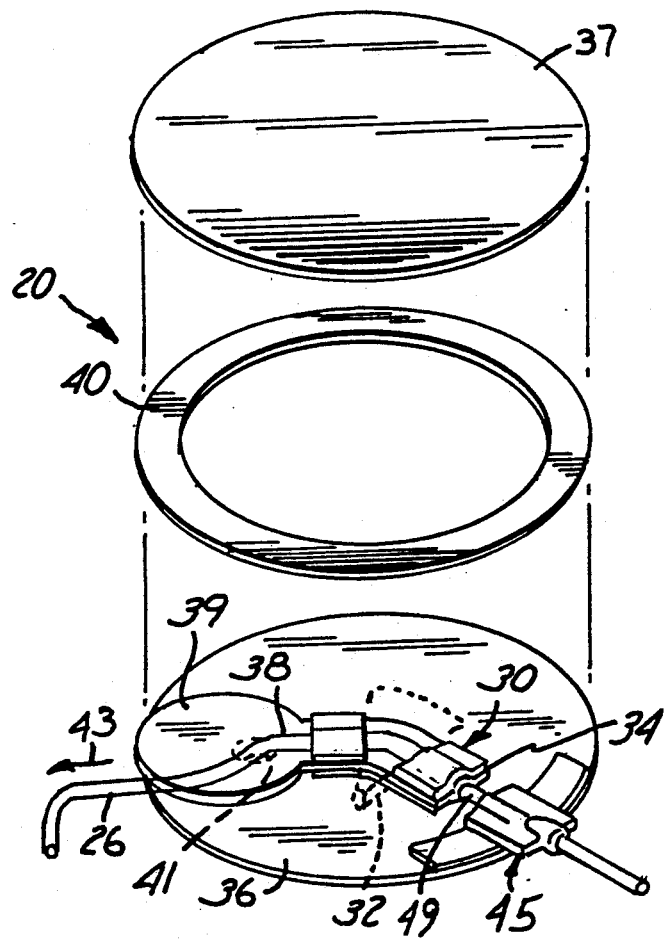
FIG. 2 is an exploded perspective view of the valve of the present invention.
Figure 3:
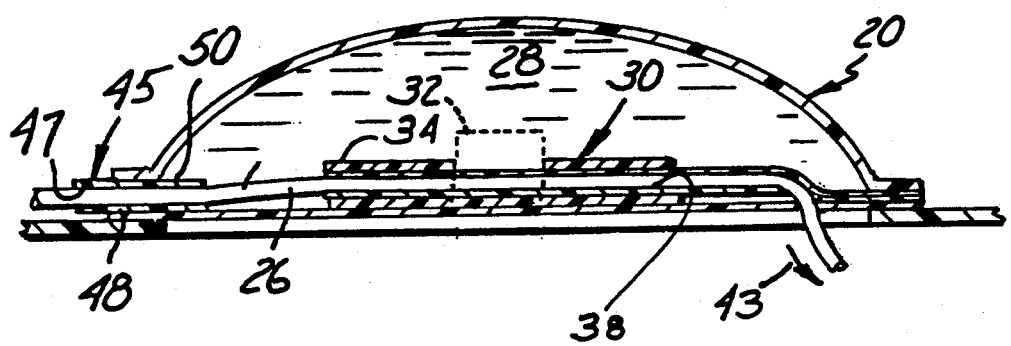
FIG. 3 is a sectional view of the valve of the present invention with a fill tube disposed therein.

The general construction of the valve 20 is best illustrated by reference to FIGS. 2 and 3. The valve 20 includes a gel filled chamber 28. A fill tube channel member 30 is disposed within the chamber 28. The channel member 30 includes an unevenly stressed portion 32 and a free end portion 34.

The gel chamber 28 is preferably constructed of an outer circular sheet 36 of vulcanized silicone elastomer joined to an inner circular sheet 37 of vulcanized silicone elastomer using a ring 40 of unvulcanized silicone elastomer to bond sheets 36 and 37 together for forming the chamber 28.

The channel member 30, through which the fill tube passes, is constructed by bonding two sheets of silicone elastomer to form the channel member 30. Prior to bonding the sheets of silicone elastomer, a removable TEFLON TM tetrafluoroethylenye fluorocarbon polymer, ribbon is placed between the two sheets to form a fill tube channel 38 into which the fill tube is positioned. Once the two sheets of silicone elastomer are bonded to form the channel member 30 and the channel 38, the TEFLON TM tetrafluoroethylene fluorocarbon polymer ribbon is removed.

The valve further includes a fill tube entry member 39 having a fill tube passage opening 41. The member 39 attaches channel member 30 to the sheet 36 and provides an access opening into the fill tube passage.

To form the unevenly stressed portion 32, the channel member 30 is stretched as indicated by arrows 35 in FIG. 4. After the channel member 30 is stretched, an unstretched sheet 42 of silicone elastomer is attached to one side of the channel member 30 over the channel 38 and first and second pieces 44 and 46 of unstretched silicone elastomer are attached on the opposite side of the channel 38 from the sheet 42.

The unstretched sheet 42 of silicone elastomer is positioned over a selected section of the fill tube channel 38. The pieces 44 and 46 are spaced apart and also overlie the channel 38 on an opposite side from the sheet 42. The spacing of the pieces 44 and 46 define the boundaries of the unevenly stressed portion 32, that is, the portion of the sheet 42 which is not opposed by either pieces 44 or 46. It will be appreciated that bonding pieces 44 and 46 overlying the fill tube channel 38 in opposing relationship to the piece 42 while the fill tube channel 38 is in a stretched condition will result in an unevenly stressed state in portion 32. The layer of elastomer in portion 32 will relax and contract since that portion is not being restrained in a stretched position.

Figure 5:
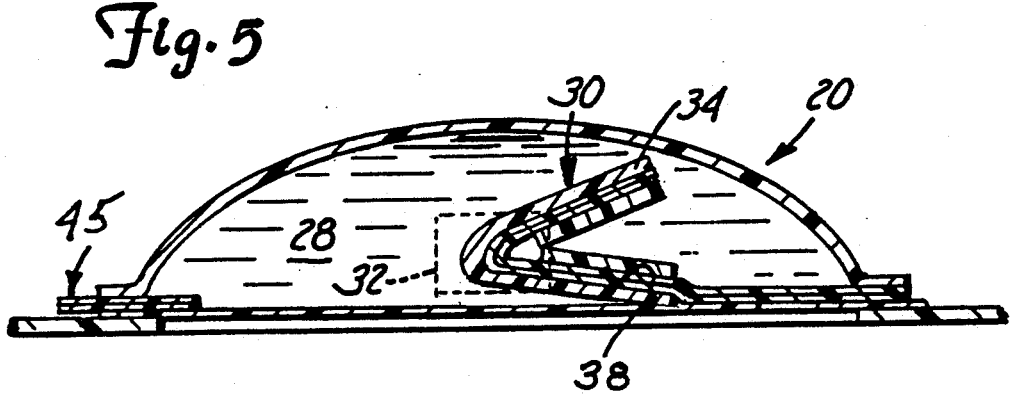
FIG. 5 is a sectional view of the valve of the present invention with the fill tube removed.

The piece 42 and the pieces 44 and 46 when bonded to the stretched channel member 30 restrain the channel member surrounding the channel from relaxing. The portion 32 between the pieces 44 and 46 which is not so restrained will relax and contract when the channel member 30 is released or when the fill tube is withdrawn. The portion 32, due to the uneven stresses, flexes such that the fill tube channel 38 folds over on itself, as illustrated in FIG. 5. The folding over of the fill tube channel causes the two layers of silicone in the portion 32 to come in contact with each other along their inner surfaces, that is the surfaces forming the channel wall resulting in a closure of the channel.

Even when the fill tube has been disposed in the fill tube channel 38 over a lengthy period of time, the folding action caused by the unevenly stressed portion 32 will flatten the fill tube channel. The gel in the chamber 28 provides an additional seal. The gel is a partially cross-linked, unfilled, silicone elastomer that is conventionally used in the construction of mammary prostheses. The gel provides both a static and a dynamic sealing mechanism.

In the static sealing mechanism, once the fill tube is removed from the fill tube channel, the opening of the end portion 34 of the fill tube channel comes into direct contact with the gel. The presence of the gel acts as a further barrier to leakage.

The dynamic mechanism includes the inclusion of cohesive gel into the fill tube channel when the fill tube is pulled from channel. As illustrated in FIGS. 2 and 3, an exposed portion 49 of the fill tube is in direct contact with the gel in the chamber 28. When the fill tube is pulled in the direction indicated by arrow 43, gel will be pulled into the fill tube channel resulting in occlusion of the channel by the gel.

A further sealing mechanism 45 is provided by the valve of the present invention. The sealing mechanism 45 is located along the periphery of the valve and provides the opening through which the fill tube extends into the inflation chamber 24 of the prosthesis. The mechanism 45 includes a fill tube channel 47 defined by layers 48 and 50 of silicone elastomer that are bonded together in a conventional fashion. When the fill tube 26 is pulled, the fill tube channel 47 closes due to the elastomeric nature of silicone layers 48 and 50.

In addition, the fill tube channel 47 becomes filled with gel and the gel acts as an additional barrier to keep fluid out from the gel chamber.

Although the present invention has been described with reference to preferred embodiments, workers skilled in the art will recognize that changes may be made in form and detail without departing from the spirit and scope of the invention.

What is claimed is:

1. A valve for use in a fluid fillable implantable device with a fill tube, the valve comprising:
    a main body portion having a channel for receiving the fill tube wherein the channel is defined by first and second elastomeric layers and wherein the first elastomeric layer is restrained in a stretched state along a selected distance and the second elastomeric layer is restrained in first and second spaced apart areas with a third area there-in-between in an unrestrained state, the first, second and third areas being in opposing relationship from the restrained area of the first layer such that when the fill tube is withdrawn from the channel, the first and second elastomeric layers fold in the third area occluding the fill tube channel.

2. The valve of claim 1 and further including: a gel-filled chamber; and wherein the main body portion is disposed in the gel-filled chamber.

3. An implantable device comprising:
    a shell defining an inflatable chamber;
    a fill rube for transporting fluid to or from the inflatable chamber;
    a valve including a main body portion having a channel for receiving the fill tube and wherein the main body portion has an unevenly stressed section that includes a selected section of the channel and wherein the unevenly stressed section is stressed so that the selected section of the channel folds back occluding the channel when the fill tube is not within the channel; and
    wherein the valve further includes a gel-filled chamber and the main body portion is disposed in the gel-filled chamber.

4. The device of claim 3 wherein the main body portion is constructed of at least first and second elastomeric layers and wherein the selected section is unevenly stressed by first and second spaced apart areas being restrained in a stretched state and the first elastomeric layer in the selected section being restrained in a stretched state while the second elastomeric layer in the selected section is permitted to relax when the fill tube is withdrawn from the channel.

5. A valve for use in a fluid fillable and implantable device in cooperation with a fill tube, the valve comprising:
    a main body portion having a fill tube channel for receiving the fill tube, and the main body portion being constructed of at least first and second elastomeric layers and wherein the main body portion has an unevenly stressed section that includes a selected section of the channel and wherein the unevenly stressed section is stressed so that the selected section of the channel folds back occluding the channel, when the fill tube is removed from the channel; and
    wherein the valve further includes a gel-filled chamber and the main body portion is disposed in the gel-filled chamber.

6. The device of claim 5 wherein the selected section is unevenly stressed by first and second adjacent areas being restrained in a stretched state and the first elastomeric layer in the selected section being restrained in the stretched state while the second elastomeric layer in the selected section is unrestrained such that the second elastomeric layer relaxes when the fill tube is withdrawn from the channel.

7. A valve for use in a fluid fillable and implantable device in cooperation with a removable fill tube, the valve comprising:
    a valve chamber having a gel therein; and
    a valve member having a fill tube channel for receiving the fill tube and having a free end disposed within the gel such that when the fill tube is removed from the fill tube passage, the valve member flexes to flatten the fill tube passage and the gel occludes the fill tube passage providing a fluid seal.

8. An implantable device comprising:
    a shell defining an inflatable chamber;
    a fill tube for transporting fluid to or from the chamber; and
    a valve having a gel filled chamber and a valve member disposed therein, the valve member having a fill tube channel for receiving the fill tube and a free end and a section that flexes when the fill tube is removed such that the fill tube passage is flattened and the free end is occluded with gel.

* * * * *